Figure 1:
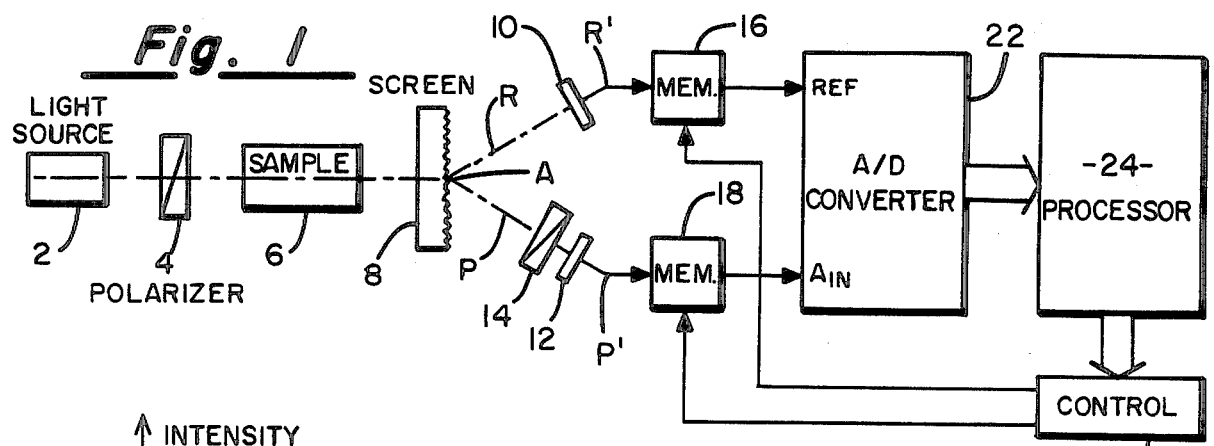

United States Patent [19]

Schmidt et al.

[11] Patent Number: 4,699,514

[45] Date of Patent: Oct. 13, 1987

[54] MULTIBEAM MEASURING DEVICE

[76] Inventors: Ulrich Schmidt, Kasinostr. 54, D-5100 Aachen; Richard Distl, Edlingerstr. 7, D-8000 Munchen 90, both of Fed. Rep. of Germany

[21] Appl. No.: 668,276

[22] PCT Filed: Feb. 27, 1984

[86] PCT No.: PCT/EP84/00050

§ 371 Date: Oct. 23, 1984

§ 102(e) Date: Oct. 23, 1984

[87] PCT Pub. No.: WO84/03357

PCT Pub. Date: Aug. 30, 1984

[30] Foreign Application Priority Data

Feb. 25, 1983 [DE] Fed. Rep. of Germany ....... 3306589
Jan. 27, 1984 [DE] Fed. Rep. of Germany ....... 3402881

[51] Int. Cl.[4] .......................................... G01N 21/21
[52] U.S. Cl. ................................................ 356/367
[58] Field of Search .............. 356/367, 435, 364, 365, 356/366, 368, 369, 370

[56] References Cited

U.S. PATENT DOCUMENTS

| | | | |
|---|---|---|---|
| 3,090,279 | 5/1963 | Chisholm | 356/354 |
| 3,283,644 | 11/1966 | Saltzman | 356/367 |
| 3,514,207 | 5/1970 | De Lang et al. | 356/367 |
| 3,518,003 | 6/1970 | Meyn | 356/367 |
| 3,646,331 | 2/1972 | Lord | 356/319 |
| 3,810,696 | 5/1974 | Hutchins | 356/435 |
| 4,266,554 | 5/1981 | Hamaquri | 356/41 |
| 4,417,812 | 11/1983 | Cserey et al. | 356/435 |
| 4,589,776 | 5/1986 | Carver et al. | 356/367 |

FOREIGN PATENT DOCUMENTS 0030610 10/1980 European Pat. Off. .
0091068 10/1983 European Pat. Off. .

Primary Examiner—R. A. Rosenberger
Attorney, Agent, or Firm—Paul L. Sjoquist

[57] ABSTRACT

Multibeam measuring device for the real time polarimetric analysis of samples (6), wherein a linearly polarized measuring beam (M) is separated after having traversed the sample (6) by means of a first separation blade (8), preferably a diffraction unit, into a reference beam (R) and at least one test beam (P). Photodiodes (10, 12) record the intensities of both partial beams between which a certain ratio is established, an analyzer (14) with fixed throughpass direction being inserted downstream of a photodiode (12). The intensity value of the test beam (P) which is standardized by the formation of the ratio as a function of the intensity of the reference beam (R) is inputted into a digital data processing unit (24). For the ratio formation, an analog-digital converter (22) is used and provided downstream of the digital data processing unit (24).

14 Claims, 8 Drawing Figures

MULTIBEAM MEASURING DEVICE

TECHNICAL AREA

The invention concerns a multibeam measuring device for the real time polarimetric analysis of samples, wherein a linearly polarized measuring beam, after having traversed the sample, is separated by means of a first beam separator into at least two partial beams representing the total beam cross-section of the measuring beam, namely a reference beam and at least one test beam. With this measuring arrangement, the intensity of the reference beam is detected by means of a first photosensitive sensor and the intensity of the test beam by means of a second photosensitive sensor. For doing this, connected in ahead of the second photosensitive sensor is an analyzer whose direction of throughpass has a predetermined, fixed orientation that is different from that of the polarizer. The signal outputs of the two photosensitive sensors are connected, for determining the polarimetric magnitudes capable of being interpreted by the sample, in particular the optical activity (e.g. the rotational value) of the sample, with the inputs of a measuring circuit.

UNDERLYING STATE OF THE ART

The aforementioned multibeam measuring device is known from the German patent DE No. 27 24 543 C2 (MULLER). In the case of the known multibeam measuring device, used as the beam separator is a dielectric separator element, namely a semi-pervious mirror. Accordingly, separation of the measuring beam into a reference and a test beam is accomplished here by reflection and transmission. Use of a beam separator of this type has the disadvantage that, because of the phase shift, the linearly polarized light impinging on the semi-perviously reflected layers is changed relative to its status of polarization, namely being converted into elliptically polarized light. Accordingly, the change of polarization status of the test beam capable of being detected by means of the analyzer stems not only from the optical activity of the sample, but rather also from the reflection at the beam separator. This has as a consequence a first systematic measurement error. Secondly, the ratio of transmitted to reflected energy in the case of a beam separator of this type is dependent upon the direction of polarization of the impinging radiation. The direction of polarization of the measuring beam impinging on the beam separator is, however, in consequence of the unknown optical activities of the sample, undefined, otherwise it would not be necessary to first determine rotation of the plane of polarization of the measuring beam by a measurement.

In the case of the multibeam measuring device known from the abovementioned German patent No. 27 24 543, the measuring circuit consists of a differential circuit disposed on the input side, with an amplifier connected downstream and an indicating and/or recording contrivance. The signal outputs of the two photosensitive sensors are here connected with the inputs of the differential circuit. However, this circuit has the disadvantage that the output signal of the differential circuit is not only a function of the angle of rotation of the plane of polarization (evoked by the optical activity of the sample), but also a function of the output intensity of the light source. Hence, it is basically not possible to determine whether a change of the output signal from the differential circuit is to be ascribed to a change in the light intensity of the light source or a change in the optical activity of the sample.

Therefore, in total, the measured value determined by means of the multibeam measuring device described is burdened with at least three systematic errors of measurement.

However, the multibeam measuring device described in the patent mentioned does have the advantage that analog signal processing apparently occurs without delay and, therefore, there is available a quasi-real time measurement. However, because of the pointertype measuring instrument apparently used in the patent that has been mentioned, slight fluctuations in measured value are no longer capable of being determined because of the inertia of the instrument. To this extent, there is present a certain measurement inaccuracy and a strongly restricted real time maasuring.

The U.S. Pat. No. 3,724,957 (TAMATE et al.) also describes a measuring device for the polarimetric analysis of samples, which has a certain similarity with the multibeam measuring device described in the aforementioned German patent. However, the multibeam measuring device known from the mentioned U.S. patent displays neither a beam separator nor does it operate in a real time process. The difficulties of beam separation are circumvented in the mentioned U.S. Pat. No. 3,724,957 in that a measuring beam with relatively large cross-section passes through the sample chamber and, next, two measurements are undertaken, by means of photosensitive sensors, at two different points of the cross-section of the measurement beam. This measure has the disadvantage that the light intensities detected by the two photosensitive sensors cannot be compared to one another, since the light beams associated to them pass through different regions of tne sample. If, for example, flowing systems or sugar mash are to be analyzed in the processing industry using the known measuring device, occurring within the sample are irregularly distributed, macroscopic regions of different turbidity, different movement condition and different refraction. Accordingly, entering into the intensity of the two different beam cross-sections are different factors for absorption when determining the rotational value. This fact leads to a systematic measurement error. For another thing, particularly in the case of using detectors that are large relative to the beam cross-section, as is necessary and provided for at least an approximated, flat integration, adulteration of the measurement value by the straying in of light from the two areas that are different for the two amplifiers (different size) is not negligible. As described in the U.S. patent, this problem cannot be eliminated by an auxiliary scatter measuring contrivance with additional photosensitive sensors, since these would not necessarily be able to be placed at the same points of the sample and, therewith, taking into consideration these disturbing magnitudes, the true value is scarcely capable of being detected.

The U.S. Pat. No. 3,724,957 teaches to form the quotients for determining the rotational value, from the intensities of the reference beam and of the test beam. This measure has the advantage that the output signal of the appropriate quotient circuit is only a function of the rotational value, in particular not a function of the output energy of the light source. This is because, when forming the quotient, possibly occurring fluctuations of the output intensity of the light source do not enter into the result of measurement, because the output intensity of the light source stands as a factor (of a product) both in the numerator and the denominator of the quotient. The quotient circuit described in the mentioned U.S. Pat. No. 3,724,957 works essentially as follows: the voltage of the photosensitive sensor, without the analyzer connected in ahead, is picked off across a fixed resistance, the voltage of the photosensitive sensor, with the analyzer connected in ahead, is picked off across a potentiometer connected as a voltage divider. Determination of the rotational value occurs by the fact that the differential signal of the two voltages is used as the input voltage for a positioning motor. The positioning motor drives the pick-off contact (slider) of the potentiometer until the difference between the voltages across the fixed resistance and across the potentiometer is equal to zero, i.e. the potentiometer is balanced out. The position of the potentiometer slider in this balanced position is a measure for the quotients of the output currents of the two photosensitive sensors. The rotational value itself is a non-linear function of the quotient of the output currents mentioned. Because of the necessity for balancing the potentiometer prior to determining the rotational value, the multibeam measuring device for real time measuring processes described in the mentioned U.S. patent is basically unsuitable. It has the same disadvantages as customary compensation methods, wherein the analyzer is adjusted until the intensities of the reference beam and of the test beam are equal. Occurring additionally is that this measuring device, whose optical activity is continually subjected to changes, is unusable for examining samples. Namely, if the optical activity of the samples to be investigated changes more rapidly than balancing of the potentiometer (capable of being carried out mechanically), then the associated (to the optical activity) rotational value cannot be determined at all.

Known from the German Offenlegungsschrift* No. 25 13 937 (FRANZ SCHMIDT & HAENSCH) is a measuring device for the polarimetric investigation of optical activity of several substances present within the same solution, by means of different wave lengths. This measuring device is not a multibeam but rather a single beam measuring device. Accordingly, it therefore displays no beam separator. Nor is it suitable for real time investigation, since it works based on the known compensation method wherein the analyzer is turned until the intensity of the light beam measured after the analyzer attains an extreme value.
*Offenlegungsschrift=laid open print, published patent application (specification) examined only as to obvious defects but not as to patentability.

Moreover, the German Offenlegungsschrift No. 25 13 937 mentioned describes insertion of a computing device in conjunction with the measuring device. The computing device, however, does not serve for calculating the number of turns associated to each substance. It serves solely for evaluating the rotational value measured in the case of different wave lengths along with control of the filters required for irradiation of the different wave lengths.

As for the rest, the individual components of several optically active components and/or substances present within the same sample cannot, as a rule, be detected by measuring as many different points of the spectrum as there are optically active substances present that are different from one another. This is because, as a rule, concentrations of unknown different substances can be measured only by employment of the anomalous Cotton effect, i.e. at the time when a wave length is irradiated, by means of which the spectrum of optical rotation dispersion shows an anomaly (resonance). Since, however, the substances are not as a rule known beforehand, the wave lengths at which the unknown substances show anomalies are likewise not known.

Known from the German Offenlegungsschrift DE No. 32 12 809 A1 (ZEISS) is an arrangement for adjusting the mean frequency of a laser tube. In the case of the known control circuit, a laser beam is bent down into a main and two auxiliary beams through a screen, preferentially a phase transmission screen with symmetrical pass profile. Here, the phase grid is laid out such that the greatest part of the intensity lies in the zeroed order. The two auxiliary beams lie in the two ± maxima of the first order. Their intensity, after passing an analyzer foil through each, is measured by a photosensitive sensor. The differential signal of the two photo voltages of the photosensitive sensors is used as the indicator for each proportion of the two polarization components of the output beam of the laser and drawn upon for stabilizing the output power and/or wave length of the laser. A polarimetric examination of the optical activity of a sample is not provided for by means of the known control arrangement and could also not be meaningfully possible.

Known from the mentioned publication, however, is that partially pervious mirrors, in the case of beam separation, exert polarizing, respectively depolarizing, effects upon the impinging light; furthermore, for avoiding this disadvantage, instead of a dielectric beam separator, hence, for example, a partially pervious mirror, use is made of a diffraction screen.

DISCLOSURE OF THE INVENTION

Starting out from the precedingly mentioned state of the art, the teaching in accordance with the invention concerns itself with the problem of improving the multibeam measuring device described, and made known in its species from the German patent No. 27 24 543 C2 retaining and developing as far as possible its existing advantages relative to its accuracy of measurement.

This task is resolved by the fact that the initially described species of multibeam measuring device displays, within its measuring circuit, for each photosensitive sensor one each after-connected short-term memory and a control circuit associated to the short-term memories, with the control circuit piloting the short-term memory for synchronous, short-term storage of the output signals of the photosensitive sensors. Furthermore, the measuring circuit displays a delay-free working division circuit that is connected on the input side with the outputs of the short-term memory and on the output side with a digital data processing contrivance for outputting the polarimetric magnitudes. Finally, the measuring circuit also displays at least one A/D converter connected ahead of the digital data processing contrivance.

Synchronous storage of the output signals of the photosensitive sensors prior to their further processing in the division circuit has the advantage, among other things, that it ensures exactly identical measurement conditions for the test beam and the reference beam and, therewith, raises measurement accuracy. Processing of the two output signals of the photosensitive sensors in one division element has the advantage that the output signal is a function only of the optical activity of the sample to be investigated and, in particular, not a function of the output intensity of the light source. The insertion of the digital data processing contrivance enables, in particular, a precise processing of the output signals of the elements connected in ahead in real time; the freedom of delay of the division circuit also serves for this.

The teaching in accordance with the invention starts out, among other things, from the consideration that the relationship between the radiation intensities ahead and after the analyzer may be expressed, for example by the following formula of Malus:

$$A = A_o \cos^2 \phi$$

whereby:
Ao: Energy of the light ahead of the analyzer
A: Energy of the light after the analyzer
$\phi$: Angle between polarization planes of the impinging light and throughpass direction of the analyzer.

By transformation of the above formula, it is now possible to determine the angle between the planes of polarization of the impinging light and of the throughpass direction of the analyzer, if Ao and A are known. The preceding equation when solved for $\phi$ becomes:

$$\phi = \arccos \sqrt{\frac{A}{Ao}}$$

In accordance with the above relationship, first determined by means of the two photosensitive sensors with after-connected division circuit is the ratio of A to Ao, or expressed differently the normalized (standardized) value of the intensity of the test beam to the intensity of the reference beam. The thusly determined, normalized value is then fed to the digital data processing contrivance for further evaluation, so that the result in real time is available directly in digital form.

A prerequisite here is that the intensities of both partial beams be equal, or at least directly proportional to one another.

The use of analog memories, e.g. sample and hold memories, as short-term memories, is suitable in particular measure for capturing the output signals coming out from both photosensitive sensors at exactly the same point in time.

Preferentially, the A/D converter is simultaneously connected also as the division circuit for the output signals of the short-term memory. For this purpose, the output of the short-term memory associated to the reference beam is connected with the reference input, and the output of the short-term memory associated with the test beam is connected with the measuring input of the A/D converter. Since the A/D converter digitalizes the value appearing at the measuring input with respect to the value appearing at the reference input, i.e. normalizes it to this latter, the thusly connected A/D converter also works as a quotient circuit—besides its function of digitalizing. This solution has the advantage of not needing an auxiliary division circuit in addition to the A/D converter. Accordingly, construction expense is reduced by this and, simultaneously, measurement accuracy is increased since, as a rule, each additional element hides within a measuring circuit the danger of measurement errors.

The construction preferentially proposed of having the digital data processing contrivance as a parallel-working multiprocessor system also serves for measurement accuracy in the real time process. This is because, through the several parallel-working microprocessors, the data throughput will be essentially increased, whereby, basically, short-term changes of the optical properties of the sample can also be determined precisely with instrumentation. Here, each microprocessor preferentially takes over exactly one functional unit, for example controlling data acquisition, calculating the optical magnitudes capable of being associated to the sample, as well as preparation of the results obtained for outputting. Specialized microprocessors are available on the market for this purpose.

By preferential utilization of a diffraction contrivance as the beam separator, the optical information obtained in each diffraction maximum is representative for the entire beam cross-section of the measuring beam passing through the sample space. Since a diffraction contrivance generally provides more than two bend maxima, the measuring beam can, in this manner, be divided into a reference beam and several test beams. If a transmission/diffraction contrivance is used as the diffraction contrivance, then each bend maximum furnishes a representative cross-section of the total measuring beam and, actually, independently of the direction of polarization of the measuring beam and without any depolarizing influence on the measuring beam. We already went into this in connection with the German Offenlegungsschrift No. 32 12 809 A1.

Preferentially utilized as a diffraction element is a screen, in particular a line screen or a replica thereof. Particularly preferred here is a phase screen, in particular a holographic phase screen which, in a particularly preferred form of embodiment, also further displays imaging properties. Preferred here is to dispose the screen relative to the measuring beam such that the pass profile of the screen lies symmetrically to the measuring beam. In this manner, a depolarizing effect of the beam separator on the measuring beam will be suppressed in particularly effective fashion.

An approximately equal signal-to-noise ratio for the reference beam and the measuring beam is preferentially achieved by using a diffraction contrivance as the beam separator, which concentrates the energy of the bent radiation essentially on the zeroed and ± maxima of the first order. Measurement accuracy is also increased by this.

Accordingly, the one photosensitive sensor will preferentially be disposed in the plus bend maximum of the first order and the other photosensitive sensor in the minus bend maximum of the first order. Assured by this is that the same intensity will be fed to the photosensitive sensor without analyzer as to the analyzer associated with the other sensor.

The initially described embodiment in accordance with the invention for the multibeam measuring device basically opens up a measurement range that comprises the magnitude toward a maximum of 90 angular degrees. Here, the analyzer is preferentially disposed such that its throughpass direction is at an angle of 45 degrees to that of the polarizer.

Because of this initial rotation, obtained is a more uniform value range of 45 angular degrees for left and right rotating (turning) substances.

Basically, the multibeam measuring device in accordance with the invention also enables an expansion of the range of measurement to a value range of ±90 angular degrees. In order to assure a high measurement accuracy here also, the beam separator, also called first beam separator in the following, separates the measuring beam into at least three partial beams, together representing the total beam cross-section of the measuring beam, namely the already mentioned reference beam, the already mentioned test beam, called first test beam in the following, and a second test beam. Within the beam path of the second test beam is likewise disposed a photosensitive sensor, called in the following third photosensitive sensor, with an analyzer connected in ahead. The analyzers associated to the two photosensitive sensors have, however, firmly predetermined throughpass directions that are different from one another. Also connected after the third photosensitive sensor is a short-term memory, with the already mentioned control circuit for controlling the short-term memory, called in the following the first control circuit, now also being laid out for the synchronous, short-term storage of the output signals of all three photosensitive sensors. Furthermore, in the case of this preferred form of embodiment, the already mentioned division circuit, or two division circuits, are connected after the short-term memories such that, capable of being formed with them, is the ratio of one of the values associated (stored in the short-term memories) (in the) to the test beams, to the stored reference value (that is the value that is stored in the short-term memory associated to the reference memory). Additionally, this preferred form of embodiment of the multibeam measuring device displays a second control circuit through means of which one of the two short-term memories associated to the test beams can selectively be piloted. Additionally, by means of the second-mentioned control circuit, the output value of the selected short-term memory is capable of being switched to the digital data processing contrivance, however, only after normalizing this output value to the stored intensity of the reference beam. This normalizing can be carried out by dividing the value of the intensity of the test beam by the value of the intensity of the reference beam.

For the purpose of guaranteeing singular results of measurement, the second control circuit preferentially displays at least one comparison stage and a switching contrivance capable of being controlled connected with its output. The comparison stage is laid out here such that it compares the intensities (stored in the short-term memory) of the test beams after their normalization to the (stored) intensity of the reference beam, e.g. through the division circuit mentioned, with a predetermined upper intensity value and a predetermined lower intensity value. The predetermined upper and lower intensity values are located within the interval from 0 to 1, with the values 0 and 1 not capable of being assumed.

In further developing the preceding form of embodiment of the multibeam measuring device in accordance with the invention, the analyzers are disposed such that the throughpass direction of the one analyzer includes an angle of 22.5 angular degrees to the throughpass direction of the polarizer, and the throughpass direction of the other analyzer includes an angle of 45 angular degrees to the throughpass direction of the first mentioned analyzer. In this case, the preselected upper intensity value equals $\cos^2 22.5°$ and the lower intensity value equals $1 - \cos^2 22.5°$.

For expanding the measurement range to a value of more than 180 angular degrees, in particular more than 360 angular degrees and guaranteeing singular, exact results of measurement within this wide measurement range, preferentially disposed ahead of the sample is a second beam separator for decoupling at least one sub-beam from the already mentioned measuring beam. The sub-beam(s) likewise pass through the sample here, with the measuring beam and all sub-beams passing over different path lengths in the sample.

The sub-beams—like the measuring beams—of the first beam separator are also separated out into a reference beam and at least one test beam. Also disposed in the beam paths of the reference and test beams of the sub-beam(s) are photosensitive sensors. Short-term memories are also connected in after these sensors. For evaluation of the measurement magnitudes detected by means of this multibeam measuring device, the digital data processing contrivance is, in this case, also laid out for calculating the rotational value(s) associated to the sub-beam(s), and joining the thusly obtained data with the rotational value associated with the measuring beam.

A precisely functioning real time measuring device, particularly in the case of analysis of kinetic processes, is advantageous. Here, it is essential to make provision for a time scale, through means of which an exact ordering of measured values and time measurement points is possible. Connected into the data processing contrivance for this purpose is a real time clock that coordinates, in particular, the time-relevant processes of data acquisition.

In another preferred form of embodiment, provided ahead of the A/D converter is an instrument amplifier that is capable of being programmed in its amplification for the purpose of increasing the precision of measurement. By this means, the digitalizing range of the A/D converter can be changed in accordance with extinctions of samples. This measure is of particular advantage in the case of a high degree of sample extinctions.

Because of its processing of results of measurement in real time, its wide range of measurement and its high degree of constancy of measurement results, the multibeam measuring device in accordance with the invention is particularly suited for industrial process control in the case of production and/or further processing of optically active substances. For this purpose, the multibeam measuring device preferentially displays an interface with which it is possibly to build a computer-computer coupling (for example a socalled LAN interface (Local Area Network). Capable of being achieved by this is an incorporation of the multibeam measuring device in accordance with the invention into a computer connection with external data processing systems.

For documentation of the results of measurement, advantageously provided is a connector for a measured value printer and/or plotter. This measure is advantageous for later evaluation of the results of measurement. By this means it is possible to graphically represent, in particular, changes in the optical magnitudes of the samples to be investigated as a function of time.

In accordance with another preferred form of embodiment of the multibeam measuring device, provided as a light source is a gas laser. The insertion of a laser permits, in conjunction with the measuring process in accordance with the invention, to also analyze the smallest of sample amounts. This characteristic is particularly in demand in enzyme research as well as for examining blood. Because of the slight divergence of the laser radiation, it is also possible to trans-illuminate large test flumes, without that there hereby exist the danger of polarizing wall reflexes. Hence, this measure enables increasing the accuracy of measurement at lowest rotational values of the entire sample. Preferentially utilized is a He-Ne laser if a relatively high light power with low cost is requested, e.g. for examination of dark sugar syrups. High line permanence power and spectral gradation—this latter by insertion of a colored grill—is offered by an argon laser. Provided for here is an adapter such that a modular type construction can be connected to any customary type commercial argon laser. The multibeam measuring device in accordance with the invention can be realized as a cost-favorable, precision polarimeter because of its small amount of expense for equipment, in the smallest of space, for example as a pocket polarimeter for diabetics. In this case, insertion of a semiconductor laser as a light source is particularly advantageous. The use of a laser diode as a light source also offers advantages in the case of analysis of substances having low absorption in the infrared range.

In order to avoid the disadvantages explained initially in connection with the German Offenlegungsschrift No. 25 13 937 when investigating (examining) substance mixtures by means of several firmly preestablished wave lengths, hence particularly for obtaining precise and predictable results of measurement in a real time process, according to another preferred form of embodiment provision is made for using as a light source for the measuring beam a source of white light with after-connected acoustico-optically tunable filters. This measure permits a spectrally triggered acquisition of polarimetric and/or photometric magnitudes. Since a measuring contrivance of this type allows a sweep duration over the entire visible spectral range of only a few milliseconds, with a sub-nanometer resolution, it is hereby possible to analyze transient events in documentary fashion, which show up in the alteration of the spectrum of the optical rotation dispersion and/or of the photometric spectrum. To be sure, acoustico-optically tunable filters are known per se and can be obtained on the market. Their use in conjunction with polarimeters, in particular multibeam polarimeters, has, however, not as yet been proposed.

In order to characterize parameters that determine the function of the acoustico-optical filter capable of being freely adjusted by any user, the control input of the acoustico-optically tunable filter is advantageously connected with a control output of the digital data processing contrivance.

A further increase in the accuracy of measurement is achieved by the fact that, for controlling at least the temperature of the sample, there are provided in the multibeam measuring device one or several Peltier elements, whereby the Peltier elements are connected with the digital data processing contrivance, in particular via a control line. Known, to be sure, is that rotation of the plane of polarization is dependent not only upon the wave length (rotation dispersion) but also upon the temperature of the irradiated sample.

As compared to customary water jacket cooling, this measure has the advantage of shorter response time and greater precision of temperature regulation. By cascading the Peltier elements, it is possible to reach temperatures of minus 80° C.—a value that is unattainable by means of water jacket cooling—wherewith is also possible the investigation of low temperature reactions.

If highly concentrated solutions and/or macroscopic particles contained therein are present, there then occur, especially in the case of analysis of long-term procedures, gravitation-occasioned dissociation phenomena that can lead to results that are difficult to interpret. From the point of view of measurement technology, the problems can be eliminated only through an integral measuring over the entire sample cross-section. This measure, however, contains system measurement errors since therewith unavoidably occurring polarizing wall reflexes would falsify the result of measurement in unpredictable fashion. The inaccuracy of measurement provoked by the preceding conditions can be advantageously eliminated by providing a contrivance for rotation of the sample chamber about the optical axis, preferentially with adjustable speed of rotation.

A further increase of the accuracy of measurement is achieved by the fact that, in accordance with a preferred form of embodiment, the first beam separator of the analyzer or analyzers and the photosensitive sensors are enclosed in an isolating vessel capable of being evacuated. In this fashion, in particular in the case of precision measurements, disturbing influences from floating particles found in the air can be excluded. The cleanest of space conditions therewith obtained inside the isolating vessel permit use of photosensitive sensors, without passivation. Prevented in this fashion are the retroreflections otherwise occurring from passivation, as well as a possible vector sensitivity, i.e. a polarization direction-dependent transmittancy for the light source.

The invention also includes a multibeam measuring device of the initially described art of the species that is characterized in that the beam separator is a deflection contrivance. This measure already procures in itself a considerable rise in measurement accuracy and, actually, independent of whether the measuring device works in real time or not.

The invention also includes a multibeam measuring device of the initially described species that displays, for expanding the measurement range while retaining exact measured values, a first beam separator that divides the measuring beam into at least three partial beams representing the entire beam cross-section, namely a reference beam, a first and a second test beam. Also disposed in the radiation path of the second test beam is a photosensitive sensor with an analyzer connected in ahead, with both analyzers having firmly predetermined throughpass directions that are different to one another.

For the comfortable utilization of the multibeam measuring device for purely photometric purposes, the multibeam measuring device displays an arrangement for the selectable, direct connection of a constant voltage source with the reference input of the A/D converter and of the output of the sensor associated to the reference beam with the measuring input of the A/D converter. Additionally, this arrangement enables shielding the remaining signals from the measurement input of the A/D converter. Relative to its measuring accuracy, the thusly obtained photometric measuring device has the same advantages as the polarimetric measuring device.

Short Description of the Drawings

Figure 3A:
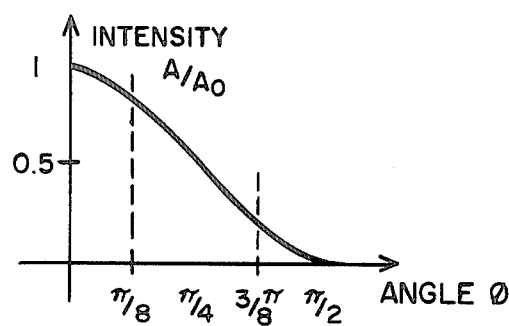
Figure 6:
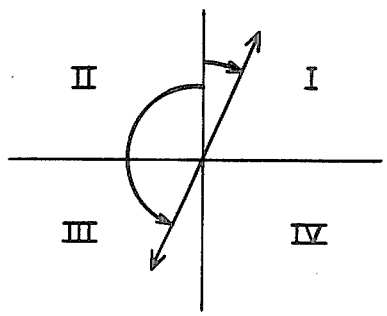
Figure 3B:
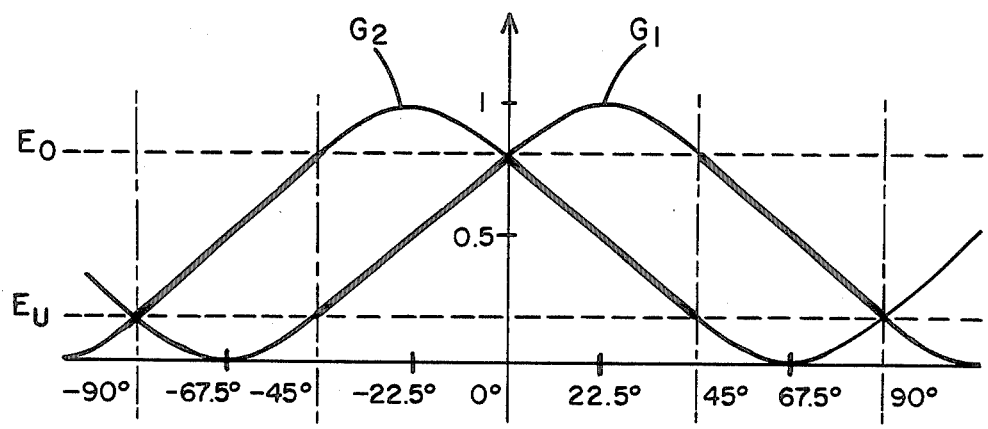
Figure 7:
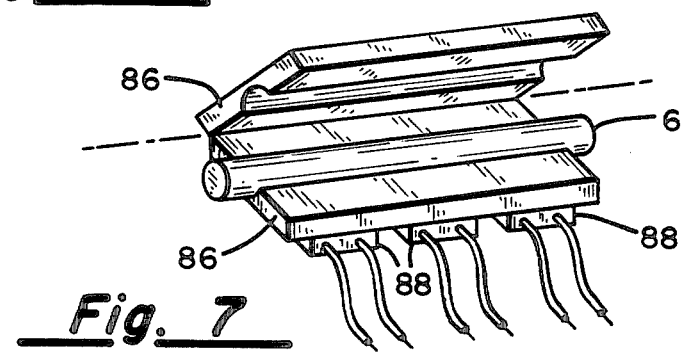
Figure 2:
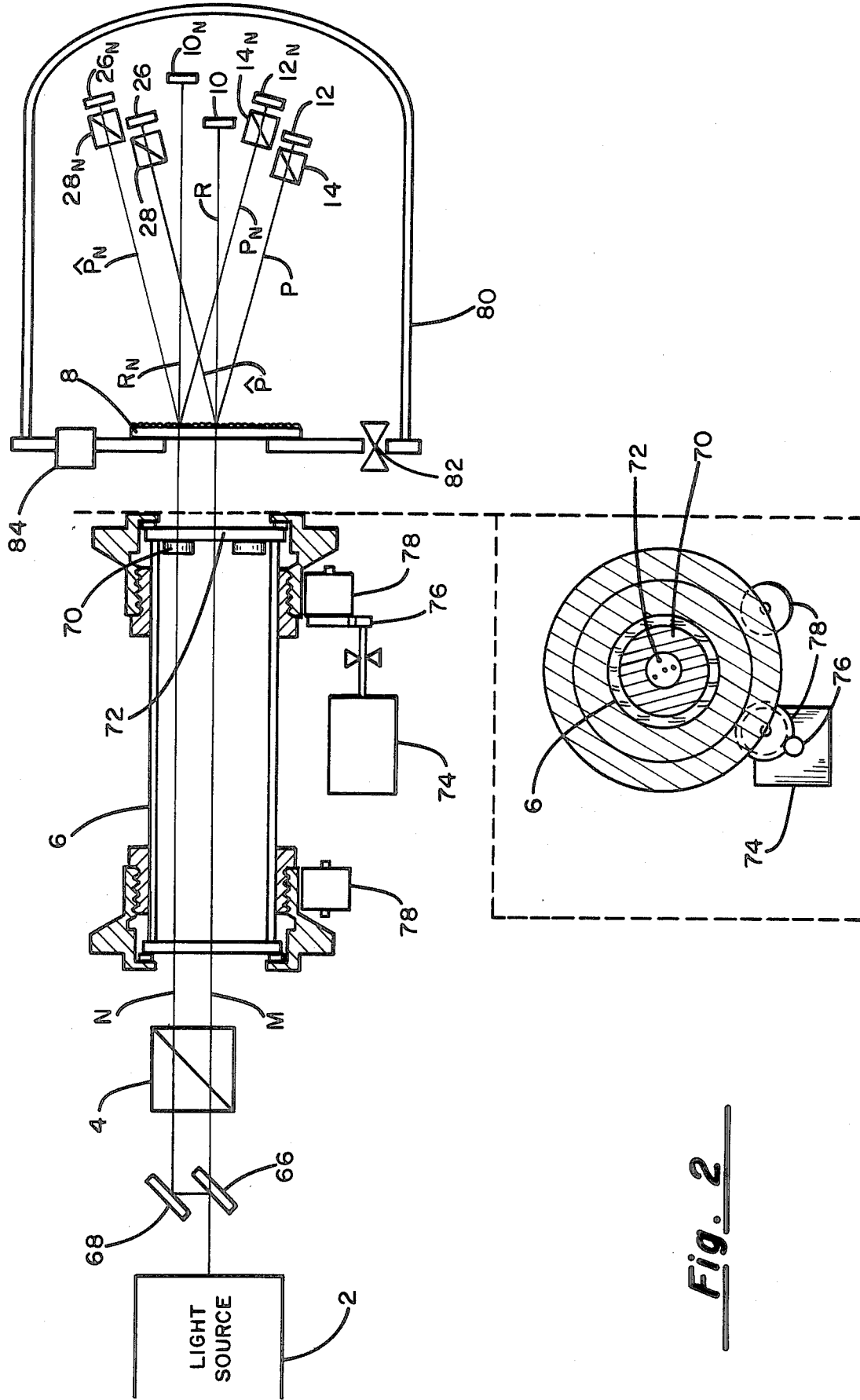
Figure 4:
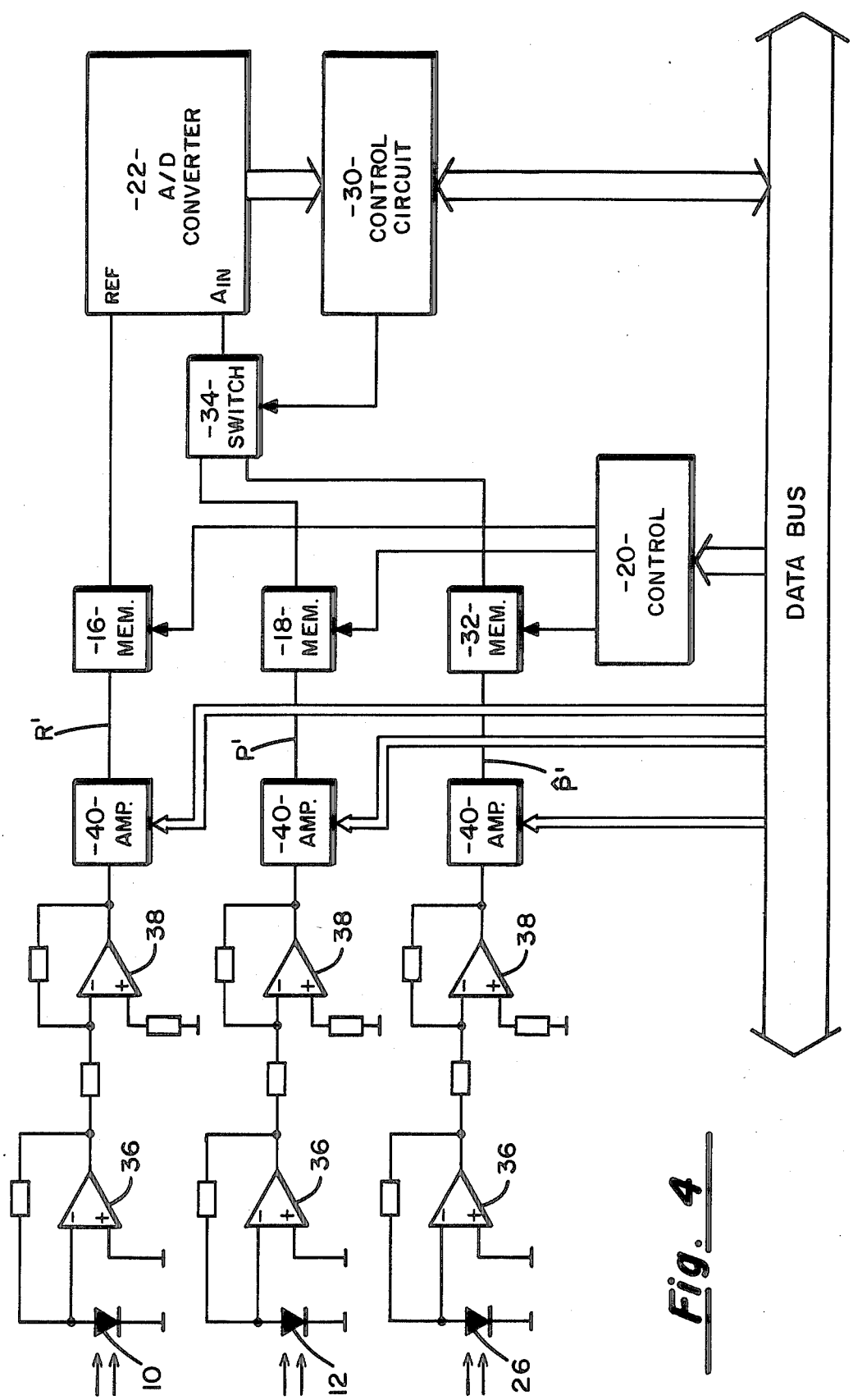
Figure 5:
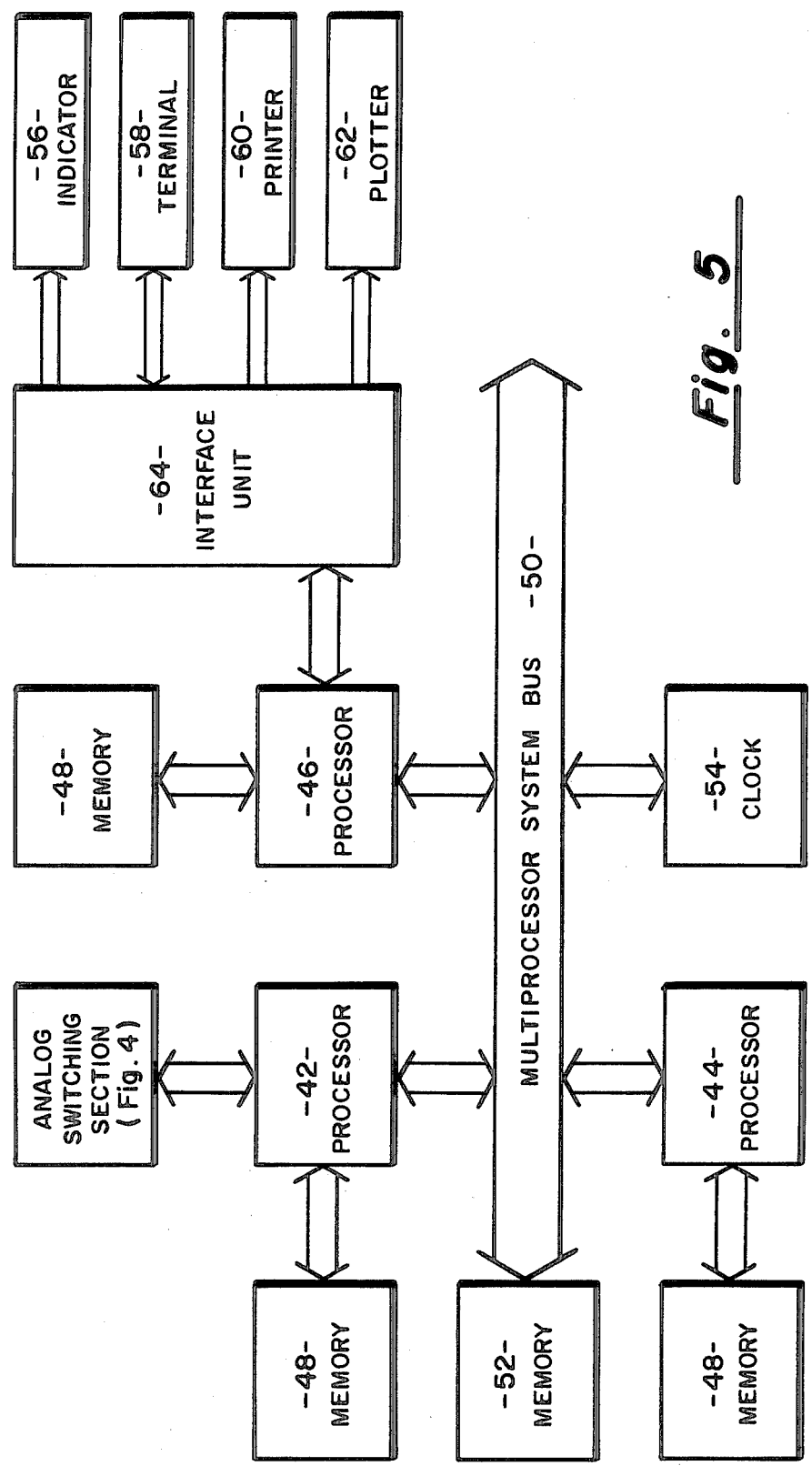

Shown in the drawings are:
FIG. 1: A greatly simplified, schematic representation of a first example of embodiment;
FIG. 2: Another example of embodiment of the invention;
FIGS. 3a and 3b: Graphs for explaining the measuring process carried out by the measuring device;
FIG. 4: An example of embodiment for an analog switching part of the measuring circuit;

FIG. 5: An example of embodiment for a digital data processing contrivance;

FIG. 6: A sketch for explaining ambiguities of the measured values;

FIG. 7: An example of embodiment for tempering the sample chamber.

Method for Executing the Invention

Used in all figures for parts that are functionally the same are the same reference numbers and/or symbols.

Illustrated in simplified and strongly schematic form in FIG. 1 is a first example of embodiment of the invention. In accordance with the example of embodiment represented, disposed one after the other along an optical axis A is a He-Ne laser as a light source 2, which sends out a measuring beam M, along with a polarizer 4, a sample chamber 6 with the sample to be analyzed contained therein, and a replica of a holographically produced phase transmission screen 8. The measuring beam is divided into two partial beams by the screen 8, namely a reference beam R and a test beam P. The two partial beams are associated to the ± bend maxima of the first order. Disposed in the bend maximum associated to the reference beam R is a first photodiode, called in the following reference photodiode 10; disposed in the bend maximum associated to the test beam P is a second photodiode, called in the following test photodiode 12. An analyzer 14 is connected in ahead of the test photodiode 12. The throughpass direction of the analyzer 14 has a preestablished, fixed orientation to that of the polarizer 4. The output signal of the reference photodiode 10, called in the following reference signal R', is fed to the input of an analog short-term memory, here a sample and hold circuit, called in the following reference short-term memory 16. In the same manner, the output signal P' of the test photodiode 12 is fed to the input of another short-term memory, here also a sample and hold circuit, called in the following test short-term memory 18. For the synchronous storage of the output signals R' and P' of the two photodiodes 10 and 12, the two short-term memories 16 and 18 are piloted synchronously by a control circuit, called in the following first control circuit 20.

The output of the reference short-term memory 16 is connected with the reference input REF of an analog/digital converter, called in the following A/D converter 22. The output of the test short-term memory 18 is connected with the measuring input AIN of the A/D converter 22. Since, in doing this, the measurement signal appearing at the measuring input AIN is continuously being digitalized such that its digital value is equal to the ratio of the measuring signal to reference signal, the A/D converter 22 simultaneously represents a division circuit. The output signal of the A/D converter 22 is consequently the digitalized quotient from measuring signal and reference signal. Expressed in other words, carried out in the A/D converter 22 is a normalizing of the measuring signal to the reference signal.

The output signal of the A/D converter 22 is fed to a digital data processing contrivance 24 that calculates the rotational value of the sample from the output signal mentioned, and possibly plots this latter through means of an after-connected plotter.

In the case of the example of embodiment represented in FIG. 1, the throughpass direction of the analyzer 14 is at an angle of 45° to that of the polarizer 4. Opened up in this fashion is a measurement range of ±45 angular degrees for right and/or left rotating optically active substances. To expand the measurement range to a value range of ±90 angular degrees, the reference photodiode 10 represented in the example of embodiment of FIG. 2 is disposed in the bend maximum of the zeroed order of the measuring beam M. In other words, in this example of embodiment, the reference beam R is associated to the aforementioned bend maximum of zeroed order. The test beam P in this example of embodiment is associated to the minus bend maximum of the first order. A third photodiode, called in the following second test photodiode 26—once again with an analyzer connected in ahead, here analyzer 28—is disposed in the plus bend maximum of the first order. The associated test beam is designated with the symbol $\hat{P}$. The throughpass directions of the two polarizers 14 and 28 include between them an angle of 45° and, relative to the throughpass direction of the polarizer, an angle of ±22.5°. Accordingly, they lie mirror-symmetrically to the throughpass direction of the polarizer 4.

The other elements represented in FIG. 2 are not at first required for explaining expansion of the measurement range to ±90°. Accordingly, they will be explained in more detail later.

The advantage of the example of embodiment described up to here in FIG. 2 is explained with the aid of FIGS. 3A and 3B. If one observes the normalized $\cos^2$ curve that has been normalized to 1, illustrated graphically in FIG. 3A, one recognizes that the function $\cos^2$ has a practically linear development within an angular range from $\pi/8$ to $\frac{3}{8}\pi$. In this connection, recalled once again is the law of Malus that has already been mentioned, according to which the intensities of the light beam ahead and after the analyzer relate to one another as the $\cos^2$ function. With an A/D conversion of the output signals of the photodiodes, therefore, the quantifying steps—or in other words the resolution—are uniformly distributed within the angular range mentioned. The uniformity of resolution guarantees a uniform precision of the results of measurement and, therewith, an overall raising of measurement accuracy.

Given in the example of embodiment in accordance with FIG. 2 was that the throughpass direction of the one analyzer is at an angle of plus 22.5° and that of the other analyzer in the angle of minus 22.5° to the throughpass direction of the polarizer 4. The throughpass function of the one analyzer, for example of analyzer 14, is described by the graph G1 reproduced in FIG. 3B, and that of the second analyzer, for example of analyzer 28, by the graph G2 reproduced in FIG. 3B. Because of the precedingly given angular ratio between the throughpass directions of the analyzers and of the polarizer, the two graphs G1 and G2 are located within the system of coordinates such that the range of values from ±90 angular degrees can be divided into four similar partial sections, with each partial section covering 45 angular degrees.

In each of these four partial sections of the range of values there is now present a practically linear section of curve of one of the two graphs. These sections of curve each correspond to the angular range from $\pi/8$ to $\frac{3}{8}\pi$ explained with the aid of FIG. 3A. By this means—as likewise explained above—guaranteed is an approximately identical resolution, but now over an angular range of ±90°.

Obtained from FIG. 3B, however, is that each graph is an ambiguous—more precisely a doubtful function—because each value of intensity of each graph can have associated to it two angular values within the range of measurement mentioned.

For resolving this problem, provided is a second control circuit 30, which is explained in more detail with the aid of FIG. 4 in conjunction with FIG. 3B.

Because of the linear transfer function of the photodiodes along with the after-connected elements, also described by a $\cos^2$ function are the possible measured values appearing at the measuring input AIN. Here, first started from is a constant intensity of the light source 2. Because of the normalizing of the measured values to the reference value in the A/D converter 22, present on its signal output connected with the second control circuit 30 are signals that are described by the graph G1 and G2. In other words, the signals described by graphs G1 and G2 are fed to the second control circuit 30. Now obtained from FIG. 3B is that there is associated, reversibly and singularly, to each of the four (each covering 45 angular degrees) partial sections of the one graph a partial section of the other graph. These partial sections lie above an upper intensity value $\epsilon_o$, respectively below a lower intensity value $\epsilon_u$. Obtained from FIG. 3A and 3B is that the upper intensity value $\epsilon_o$ is located such that it cuts off the linear partial section of the non-linear partial section of the graphs. The same applies for the lower intensity value $\epsilon_u$. Accordingly, in the example of embodiment represented, the upper intensity value $e_o$ has the value of $\cos^2 \pi/8$ and the lower intensity value has the value of $1-\cos^2 \pi/8$, respectively $\cos^2 \frac{3}{8}\pi$.

The second control circuit 30 now displays at least one comparison stage in which the output signals of the A/D converter 22 are compared with the upper and lower intensity value $\epsilon_o$ and $\epsilon_u$. The result of this comparison—simultaneously taking into consideration the origin of the normalized measured value (hence the fact whether the normalized measured value stems from the first test photodiode 12 or from the second test photodiode 26)—clearly yields the angular range within which the instantaneously measured value of rotation lies. Additionally obtained from the precedingly described comparison is which of the values associated to the two test beams lie within the range delimited by the upper and lower intensity value $\epsilon_o$ and $\epsilon_u$, in other words, therefore, which measured value is to be drawn upon for determining the rotational value. This selected measured value is then switched through from the second control circuit 30 to the digital data processing contrivance 24. Simultaneously, by means of the second control circuit 30, the information obtained therefrom is likewise conducted over the rotational value of range to the digital data processing contrivance 24.

In the example of embodiment according to FIG. 4, further provided is an analog switch 34 for sequentially switching the outputs of the short-term memories 18 and 32 on through to the measuring input AIN of the A/D converter 22. The analog switch 34 is, in turn, controlled by the second control circuit 30.

According to FIG. 4, all photodiodes are driven in the photoamperic circuit 36. Here, the signal of each photodiode 10, 12, 26 is fed, via an inverter 38, to an instrument amplifier 40 that is capable of being programmed in its amplification. The outputs of the instrument amplifier 40 are connected with the inputs of the already described short-term memories 16, 18 and 32, respectively.

The control inputs of the instrument amplifier 40 are connected with the digital data processing contrivance 24.

Represented in FIG. 5 is an example of embodiment for one configuration of the digital data processing contrivance 24. According to the example of embodiment represented, the data processing contrivance 24 is designed as a parallel-working multiprocessor system. The analog switching section represented in FIG. 4 is connected with the data processing contrivance 24 over the local data bus of a data acquisition processor 42. The data acquisition processor 42 takes over acquiring the data retrieved in the analog switching section and processes these. Furthermore, it provides all necessary control signals for the analog switching section. Provided for calculating the optical magnitudes capable of being associated to the sample 6 is a hardware type designed arithmetic processor 44; provided for preparation of the data for outputting to peripheral devices is an input/output processor 46. Each processor 42, 44, 46 is connected with a program and data memory 48 associated especially to it, via a local bus. All processors access to a common data memory 52 in which are contained data to be exchanged, over a common system bus 50. A real time clock 54 programmed for interrupt operation controls all time-relevant processes of the multiprocessor system. The peripheral devices, namely a 7-segment indicator 56, a terminal 58, a printer 60 and a plotter 62 are connected, via an interface unit 64, with the input/output processor 46.

As has been explained with the aid of FIG. 2, it is possible, through a measurement by means of a reference beam and two test beams, to detect a measurement range stretching over 180 angular degrees.

However, capable of being seen from FIG. 6 is that it is not clearly obvious from a single measurement whether the actual rotation has occurred in the first or third quadrants, in other words whether the plane of polarization was rotated left or right by an additional amount (n×180°).

The actual value of rotation can be expressed by the following formula:

$$\beta = \phi + n \times 180 \text{ degrees}$$

where:
n: a whole number
$\beta$: actual rotational value
$\phi$: measured rotational value In order to be able to determine the variable n, disposed, in accordance with FIG. 2, is a second beam separator 66 between the light source 2 and the polarizer 4. By means of the second beam separator 66, decoupled from the measurement beam M is a sub-beam N, and linked, via a mirror 68, through the polarizer 4, and finally the sample chamber 6. The measuring beam M and the sub-beam N, in the example of embodiment represented, run parallel to one another through the sample chamber 6. The sub-beam N, however, passes through inside the optically active substance over a section of path of different length than the measuring beam M, here a shorter stretch of path. For this purpose, disposed in the radiation (beam) path of the sub-beam N is an optically neutral, in particular optically inactive, light-permeable substance of predetermined thickness. Since the sample chamber 6, as will be explained further later, is to rotate about the optical axis A, this substance is designed as a ring 70 and disposed coaxially to the measuring beam M. In particular, the ring 70 is here attached to the output window 72 of the sample chamber 6.

After running through the sample chamber 6, the sub-beam N also comes up against the phase/transmission line screen 8 and, like the measuring beam M—is also split there into a reference beam $R_N$ and two test beams $P_N$ and $\hat{P}_N$. The two test beams $P_N$ and $\hat{P}_N$ correspond here to the $\pm$ bend maxima of the first order; the reference beam $R_N$ corresponds to the bend maximum of the zeroed order. Disposed, in turn, in the bend maximum of the zeroed order of the sub-beam N is a reference photodiode $10_N$; disposed in the $\pm$ bend maxima of the first order of the sub-beam N are the photodiodes $12_N$ and $26_N$. Also connected in ahead of the two test photodioes $12_N$, $26_N$ is again one each analyzer $14_N$ and $28_N$, respectively.

Accordingly, the sub-beam N, as seen from the point of measurement instrumentation, is handled basically in the same fashion as the measuring beam M. This also applies—as explained in more detail in the introductory description—for the elements of the measuring circuit connected in after the photodiodes of the sub-beam.

The rotational values of the sample, measured with the measuring and sub-beam, are directly proportional to the distance traversed by them inside the sample. Accordingly, it is possible to set up a relationship between the length of the paths passed over and the actual rotational values in the case of these path lengths, namely $$\beta_2/L_2 = \beta_1/L_1$$

where:
L1: Path length of the measuring beam N inside the sample
L2: Path length of the sub-beam N inside the sample
$\beta_1$: Actual rotational value in the case of path length $L_1$
$\beta_2$: Actual rotational value in the case of path length $L_2$ By substitution of the above mentioned general formula, one obtains the following relationship:

$$\phi_2 + n_2 \times 180° = L_2/L_1 \, (\phi_1 + n_1 \times 180°)$$

where:
$\phi_1$: measured rotational value witha length L1
$\phi_2$: measured rotational value witha length L2.

In doing this, ambiguities occur if n1 is different from n2, i.e. if within the path length $\Delta L = |L_1 - L_2|$ *a rotation of more than* 180° takes place.

If one selects L1 and L2 such that a rotation within the distance $\Delta L$ does not exceed 180°, $n_1$ and $n_2$ can then be said equal to one another, hence, $n_1 = n_2 =: n$.

By substitution and transformation of said relationships, one obtains:

$$n \times 180° = \frac{\frac{L2}{L1} \times \phi_1 - \phi_2}{1 - \frac{L2}{L1}}$$

Substitution of the thusly obtained value for n then yields:

$$\beta_1 = \phi_1 + \frac{\frac{L2}{L1} \phi_1 - \phi_2}{1 - \frac{L2}{L1}}$$

If one starts out from the standard length of the test flume for the sample of 100 mm for $L_1$ and, e.g., 99 mm for $L_2$, then, within a path length of $\Delta L = 1$ mm, the sample would need to cause a rotation of the polarization plane of more than 180° in order to introduce an ambiguity into the range of measurement. Since substances with this type of high rotational capability has not, however, as yet been demonstrated, one can start out from the fact that, with the above described measuring procedures, all substances can be singularly analyzed and, actually, in real time.

With the values of $L_1$ and $L_2$ given, obtained, for example, is a measurement range with a maximum of $\pm 18\,000$ angular degrees.

In the case of the example of embodiment represented in FIG. 2, further provided is an electrical motor 74 that sets the sample chamber 6 into rotation about the optical axis via a gear drive 76. The sample chamber 6 is journaled here on four roller bearings 78, of which, however, only one is turned directly by the gear drive 76.

The phase/transmission line screen 8, all photodiodes and analyzers are disposed inside an isolating container 80 that is capable of being evacuated. The isolating container 80 is equipped with a vacuum valve 82 and a feedthrough 84 for the measuring cable.

According to FIG. 7, the sample chamber 6 is jacketed about by a heat conducting adapter 86 which, in turn, is connected in heatconducting fashion with a Peltier element 88.

We claim:

1. A multibeam measuring device for the polarimetric, real time analysis of a sampel (6), comprising
   (a) means (4) for linearly polarizing a measuring beam (M) and passing said measuring beam (M) through the sample;
   (b) a first beam separator means (8) for separating said measuring beam (M) into at least three partial beams representing the total radiation cross-section of the measuring beam (M), comprising at least a reference beam (R), a first test beam (P), and a second test beam ($\hat{P}$);
   (c) means for impinging the reference beam (R) upon a first photosensitive sensor (10), and for impinging the first test beam (P) upon a second photosensitive sensor (12), and for impinging the second test beam ($\hat{P}$) upon a third photosensitive sensor (26);
   (d) a first analyzer (14) interposed to receive the first test beam (P) ahead of the second photosensitive sensor (12), said first analyzer (14) having a direction of throughpass which is a preselected fixed orientation different from the orientation of said means (4) for linearly polarizing;
   (e) a second analyzer (28) interposed to receive the second test beam ($\hat{P}$) ahead of the third photosensitive sensor (26), said second analyzer (28) having a direction of through pass which is a preselected fixed orientation different from the orientation of said first analyzer (14);
   (f) a measuring circuit having respective inputs connected to receive signals from said first, second and third photosensitive sensors (10, 12, 26) and having means for developing signals representative of the respective polarimetric magnitude associated with said sample (6), including (1) a respective first, second and third short term memory (16, 18, 32), each connected to receive a signal from a respective first, second or third sensor (10, 12, 26), and a first control circuit means for synchronizing the signals into each short term memory;

(2) at least one real time division circuit (22) connected to said short term memories, having means for forming at least one ratio signal by developing the ratio of the signals from the second to the first short term memory and/or the ratio of the signals from the third to the first short term memory;

(3) a second control circuit (30) connected to said real time division circuit (22) for selectively gating the at least one ratio signal to a second control circuit output, said second control circuit having at least one comparison stage and a controllable switching device connected to said second control circuit output, whereby the at least one comparison stage compares the intensities of the first and second test beams stored in the second and third short term memories after the said at least one ratio signal has been formed, by comparing the said at least one ratio signal with a preestablished upper intensity value Eo and a preestablished lower intensity value Eu, said at least one comparison stage developing an output signal for controlling the switching of the said at least one ratio signal to a data processor;

(4) a data processor (24) connected to the second control circuit (30) output, and having means for storing and outputting said at least one ratio signal in digital form.

2. The device of claim 1, wherein each of said short term memories (16, 18, 32) further comprise an analog sample and hold circuit.

3. The device of claim 1, wherein said at least one real time division circuit (22) further comprises an analog to digital (A/D) converter having at least two inputs.

4. The device of claim 3, wherein the A/D converter inputs further comprises a reference input (REF) and a measuring input (AIN) and the reference input is connected to a short term memory associated with the reference beam (R) and the measuring input is connected to a short term memory associated with a test beam (P,$\hat{P}$).

5. The device of claim 3, further comprising an instrument amplifier disposed ahead of said A/D converter, said amplifier being programmable in amplication.

6. The device of claim 1, wherein said first beam separator means (8) further comprises a diffraction device.

7. The device of claim 6, wherein said diffraction device further comprises a phase screen.

8. The device of claim 7, wherein said phase screen further comprises a holographically produced screen with imaging characteristics.

9. The device of claim 7 or 8, wherein the phase screen further comprises a pass profile which is disposed symmetrically to said measuring beam (M).

10. The device of claim 1, wherein the first and second analyzers (14, 28) further comprise one analyzer having a throughpass direction angle of 22.5° relative to the passthrough direction the means (4) for linearly polarizing, and the other analyzer having a throughpass direction angle of 45° relative to said one analyzer.

11. The device of claim 1, further comprising means for expanding the measurement range to an amount greater than 180°, comprising (a) a second beam separator means (66) disposed ahead of said sample (6), having means for decoupling at least one sub-beam (N) from the measuring beam (M), and for passing said at least one sub-beam (N) through said sample over a path having a different length than the path of said measuring beam (M);

(b) means for dividing said at least one sub-beam (N) by said first beam separator means (8) into a reference beam ($R_N$) and at least one test beam ($P_N$, $\hat{P}_N$);

(c) means for impinging the reference and test beams ($R_N$, $P_N$, $\hat{P}_N$) upon further photosensitive sensors ($10_N$, $12_N$, $26_N$) respectively associated with each of the beams;

(d) a short term memory connected to each of the sensors ($10_N$, $12_N$, $26_N$); and (e) means for processing in said data processor (24) values associated with the outputs of said sensors ($10_N$, $12_N$, $26_N$), including calculating rotational values associated with said sub-beams and combining the results thereof with calculated rotational values associated with the measuring beam (M).

12. The device of claim 1, further comprising a semiconductor laser means for generating said measuring beam (M).

13. The device of claim 1, further comprising a white light source means for generating said measuring beam (M), said white light source having acoustico-optical tunable filters having respective control inputs connected to said data processor (24).

14. The device of claim 1, further comprising at least one temperature controller means for controlling the temperature of at least one element, said temperature controller means including a Peltier element controllably driven by said data processor (24).

* * * * *